United States Patent
Stein et al.

(10) Patent No.: US 10,668,669 B2
(45) Date of Patent: Jun. 2, 2020

(54) SYSTEM AND METHOD FOR MANUFACTURING A BAG FOR MEDICAL PURPOSES

(71) Applicant: KIEFEL GMBH, Freilassing (DE)

(72) Inventors: Bernd Stein, Kirchanschöring (DE); Rupert Gschwendtner, Bad Reichenhall (DE)

(73) Assignee: Kiefel GmbH, Freilassing (DE)

( * ) Notice: Subject to any disclaimer, the term of this patent is extended or adjusted under 35 U.S.C. 154(b) by 105 days.

(21) Appl. No.: 15/551,858

(22) PCT Filed: Feb. 19, 2016

(86) PCT No.: PCT/DE2016/000061
§ 371 (c)(1),
(2) Date: Aug. 17, 2017

(87) PCT Pub. No.: WO2016/131440
PCT Pub. Date: Aug. 25, 2016

(65) Prior Publication Data
US 2018/0065315 A1 Mar. 8, 2018

(30) Foreign Application Priority Data
Feb. 20, 2015 (DE) .................. 10 2015 002 006

(51) Int. Cl.
*B29C 65/00* (2006.01)
*B26D 7/00* (2006.01)
(Continued)

(52) U.S. Cl.
CPC ............ *B29C 65/7841* (2013.01); *A61J 1/10* (2013.01); *A61J 1/1475* (2013.01); *B26D 3/16* (2013.01);
(Continued)

(58) Field of Classification Search
None
See application file for complete search history.

(56) References Cited

U.S. PATENT DOCUMENTS

| 3,214,312 A | 10/1965 | Gattrugeri |
| 3,432,986 A | 3/1969 | Schneider et al. |

FOREIGN PATENT DOCUMENTS

| BE | 883828 A1 | 10/1980 |
| DE | 102010050136 A1 | 12/2011 |

(Continued)

OTHER PUBLICATIONS

International Preliminary Report on Patentability for Application No. PCT/DE2016/000061 dated Jan. 25, 2017, 4 pages (English translation).

(Continued)

*Primary Examiner* — Linda L Gray
(74) *Attorney, Agent, or Firm* — Stinson LLP (57) ABSTRACT

The aim of the invention is to avoid the risk of contamination of a bag for medical purposes, in particular to significantly reduce the amount of residual particles of material during the cutting of a tube for access to the bag. The invention proposes a system (1) for producing a bag for medical purposes comprising a tube transfer station (2) having transfer means (3) for transferring a tube (11), which is being transported towards the tube transfer station (2), to a holder (10) and for separating there a tube section (17) transferred to the holder (10) from a remainder (18) of the tube (11), in order to then render the separated tube section (17) connectible to two film layers to form an access to the bag. The tube transfer station (2) comprises at least one air nozzle (55, 57), and an effective area (58) of the at least one air nozzle (55, 57) is directed onto a designated location (20) for separation such that a forced air flow (56) in the (Continued)

designated location (20) forced by air blown out and/or drawn in can be adjusted for separation.

27 Claims, 5 Drawing Sheets

(51) Int. Cl.
| | |
|---|---|
| *B26D 3/00* | (2006.01) |
| *A61J 1/00* | (2006.01) |
| *A61M 39/00* | (2006.01) |
| *B29C 65/78* | (2006.01) |
| *B26D 7/18* | (2006.01) |
| *B26D 3/16* | (2006.01) |
| *A61J 1/10* | (2006.01) |
| *A61J 1/14* | (2006.01) |
| *A61M 1/02* | (2006.01) |
| *A61M 39/14* | (2006.01) |
| *A61M 39/18* | (2006.01) |
| *A61M 39/08* | (2006.01) |
| *B29C 65/02* | (2006.01) |
| *B29L 31/00* | (2006.01) |

(52) U.S. Cl.
CPC ......... *B26D 7/1854* (2013.01); *B26D 7/1863* (2013.01); *B29C 65/78* (2013.01); *B29C 66/02241* (2013.01); *A61M 1/0209* (2013.01); *A61M 39/146* (2013.01); *A61M 39/18* (2013.01); *A61M 2039/087* (2013.01); *A61M 2207/10* (2013.01); *B26D 3/164* (2013.01); *B29C 65/02* (2013.01); *B29C 66/4742* (2013.01); *B29L 2031/7148* (2013.01)

(56) References Cited

FOREIGN PATENT DOCUMENTS

| | | |
|---|---|---|
| EP | 1500451 A2 | 1/2005 |
| EP | 3006007 A1 | 4/2016 |

OTHER PUBLICATIONS

International Search Report and Written Opinion for Application No. PCT/DE2016/000061, dated Aug. 5, 2016, 15 pages.

SYSTEM AND METHOD FOR MANUFACTURING A BAG FOR MEDICAL PURPOSES

CROSS REFERENCE TO RELATED APPLICATIONS

This application is a U.S. national stage application of PCT application PCT/DE2016/000061, filed Feb. 19, 2016 and claims priority to German application 10 2015 002 006.4 filed Feb. 20, 2015, each of which is hereby incorporated by reference in its entirety.

FIELD OF THE DISCLOSURE

The invention relates to a method for manufacturing medical bags and to a plant for manufacturing medical bags.

BACKGROUND

Generic plants and methods for separating an individual piece of tube, which will later become part of a port to a medical bag, from a tube, are sufficiently known from the state of the art. In particular, it is known to lead a tube to a tube plug-in or tube transfer station and to separate it there into individual tube pieces.

During this process, individual tube pieces are cut off from an "endless tube" so that they can then be provided individually to the films. For this purpose, an end of this endless tube is fed to a holder and fixed into place there so that a tube piece which has been cut off from a residual tube of the endless tube is being held by the holder. The tube pieces separated in this manner are then placed between two films by means of an accordingly adapted apparatus and are then welded together with the two films to form a medical bag.

It is understood that already during manufacturing of such medical bags, a contamination by dirt or material particles formed by the process itself or the like must under all circumstances be avoided in order to reduce or completely prevent the risk of contamination of the medical product which is later stored in the medical bag.

SUMMARY

In one aspect, a plant for manufacturing a bag for medical purposes includes a tube transfer station with a transfer means for transferring a tube fed to the tube transfer station to a holder and for separating there a tube piece transferred to the holder from a residual tube of the feeding tube, so as to make the separated tube piece subsequently connectable to two film layers for forming an access on the bag. The tube transfer station includes at least one air nozzle. An action area of the at least one air nozzle is directed at a designated place for cutting, so that an air flow forced by air which has been blown out and/or aspirated can be adjusted for cutting at the designated place.

In another aspect, a method for manufacturing a bag for medical purposes includes transferring a tube fed to a tube transfer station to a holder by a transfer means for separating there a tube piece transferred to the holder from a residual tube of the feeding tube so that the tube piece is subsequently connected to two film layers for forming an access to the bag. During separation of the tube piece from the residual tube of the feeding tube, at least one air nozzle is operated with a pressure difference means for producing an overpressure and/or a vacuum at the air nozzle, with an action area of the at least one air nozzle being directed onto the designated place for cutting. The pressure difference means is operated during cutting, such that an air flow forced by air which is blown out and/or aspirated is adjusted at the designated place for cutting.

DETAILED DESCRIPTION

The invention refers, on the one hand, to a plant for manufacturing a bag for medical purposes, comprising a tube transfer station with a transfer means for transferring a tube fed to the tube transfer station to a holder and for separating there a tube piece transferred to the holder from a residual tube of the feeding tube, so as to subsequently make the separated tube piece connectable to two film layers to form an access to the bag.

On the other hand, the invention refers to a method for manufacturing a bag for medical purposes in which a tube fed to a tube transfer station is transferred to a holder for separating there a tube piece transferred to the holder from a residual tube of the feeding tube, so as to subsequently connect the tube piece to two film layers to form an access to the bag.

The invention is based on the task of further developing in particular generic plants for manufacturing a bag for medical purposes such that the danger of contamination, in particular caused by an access to the bag which is formed by a tube, is reduced.

The object of the invention is achieved by a plant for manufacturing a bag for medical purposes, comprising a tube transfer station with a transfer means for transferring a tube fed to the tube transfer station to a holder and for separating there a tube piece transferred to the holder from a residual tube of the feeding tube, so as to subsequently make the separated tube piece connectable to two film layers to form an access to the bag, the tube transfer station comprising at least one air nozzle and an action area of the at least one air nozzle being directed at a defined region for cutting so that an air flow forced by air which has been blown out and/or aspirated can be adjusted at the defined region for cutting.

By equipping the tube transfer station with at least one such air nozzle, any residual tube material particles can be removed from the cutting region (defined region) or from the tube piece and also from the residual tube of the feeding tube by the created air flow when the tube piece is separated from the feeding tube.

Thus, the danger of contamination of the tube piece and thus also of the subsequent port of the medical bag and of its contents by residual tube material particles is significantly reduced if not even entirely excluded.

It is also advantageous for the tube transfer station to comprise an air ionization device for sterilizing substantially the cut tube piece and, if possible, also the residual tube directly at the tube transfer station.

Preferably, this air ionization device is assigned in construction to the at least one air nozzle so that the air flowing from this air nozzle can be ionized.

For forcing an air flow, the at least one air nozzle can be connected fluidically to a pressure difference means by means of a corresponding tube device, so as to create an overpressure and/or a vacuum.

Preferably, the at least one air nozzle has a pressure difference means for creating an overpressure and/or a vacuum at the air nozzle so that in the area of the pressure difference means, an air flow forced by air which has been blown out and/or aspirated can be adjusted for cutting in the defined region. Thus, an additional tubing is not necessary whereby a corresponding assembly can be made even more compact. Furthermore, even an existing tube transfer station can easily be retrofitted in this manner.

It is understood that the at least one air nozzle can be embodied such that air is both blown out and aspirated by it, for instance by providing the at least one air nozzle with two spatially separated air channels.

A preferred embodiment provides for two air nozzles, one being adapted for blowing out air and a second nozzle being adapted for aspirating air. On the one hand, more space is required for this alternative; on the other hand, the two air channels can be further separated in this manner.

It is especially advantageous if the defined region for cutting is arranged between the air nozzles. For this purpose, air can be blown on the cutting region from one side by means of a first air nozzle of the air nozzles, whereas from a different side, air is aspirated from the cutting region by means of a second air nozzle of the air nozzles.

In this manner, it is possible to blow away, on the one hand, any residual tube material particles from the separated tube piece and from the end of the feeding tube facing this tube piece and, on the other hand, to immediately aspirate these residual tube material particles which have been whirled up or blown away, respectively, so that also the environment of the tube transfer station is immediately protected from contamination by any residual tube material particles which may whirl around.

For a more variable setting of the tube transfer station in terms of cutting or separating processes, it is advantageous if the at least one air nozzle is displaceable in particular with respect to the defined region.

For being able to remove, i.e. aspirate, the residual tube material particles from the tube transfer station substantially directly at the place where they are produced, it is particularly advantageous if at least the second air nozzle for aspirating air is arranged in a sluable manner at the tube transfer station.

Such a sluability of the second air nozzle can be easily guaranteed by means of construction at the tube transfer station if the second air nozzle for aspirating air is arranged at a sluable holding device for holding a cutting means for cutting the feeding tube.

The sluable holding device designed in this manner can be manufactured for instance in a 3D printing process.

By way of example, such a sluable holding device is explained in the following in connection with a knife for cutting the feeding tube, the knife being arranged at a cutting head in a sluable or foldable manner.

In addition, the production of residual tube material particles can already be significantly reduced or even completely avoided, if the tube transfer station has a tube pulling means on the holder side and a tube pulling means on the other hand which are adapted to apply tensile forces between the cut tube piece and the residual tube of the feeding tube, while cutting takes place.

In the present application, the tube transfer station is particularly designed such that a tube piece which has been transferred to the holder and is to be cut is at least temporarily fixed into place on the holder before cutting by a tube pulling holding means.

Furthermore, by means of the tube transfer station, tensile forces can be applied to the clamped and fixed tube, so that the feeding tube can be provided at the tube transfer station in pretensioned form at least in a tube area between the transfer means and the holder; in this manner, in turn, the tube piece transferred at the holder can be separated from the residual tube on the side of the transfer means, such that by the actual cutting process, substantially less residual tube material particles are released into the environment.

In other words, this means that during cutting, less residual tube material particles are produced by the cutting process, thus reducing the risk that such residual tube material particles can contaminate the separated tube piece on the one hand, but also the residual tube of the feeding tube on the other hand; which reduces the danger that such residual tube material particles can reach the medical product to be stored in the medical bag.

In other words: with the present invention, it is possible to perform a very clean cut at the feeding tube.

Therefore, the object of the invention is also achieved by a method for manufacturing a bag for medical purposes, wherein a tube fed to the tube transfer station is transferred to a holder so that a tube piece transferred to the holder is separated there from the residual tube of the feeding tube so that the tube piece is subsequently connected to two film layers to form an access to the bag, the method being characterized in that in particular the following steps are performed: first, feeding the feeding tube to the holder; secondly, tightly holding the feeding tube on the tube piece to be cut on the side of the holder by means of a tube pulling holding means; thirdly, longitudinal drawing of the feeding tube between the tube pulling holding means and a feeding device so that a tensile force acts on the defined region for cutting; and fourthly, separating the tube piece from the residual tube of the feeding tube.

With this proposed method, it is possible to perform a very clean cut at the feeding tube, where substantially less residual tube material particles are produced and released into the environment during cutting.

Depending on the tube transfer station, in particular on the transfer means, the holder can be of nearly any type of construction.

The end of the feeding tube which faces the holder or the tube piece to be separated, respectively, can be transferred to the holder very easily with regard to construction, if the holder has a spike which the feeding tube can at least partially be plugged on.

Therefore, the tube transfer station can also be termed a tube plug-on station; although it is explicitly pointed out here that plugging is not necessary to implement the invention, but that mere transfer of the tube end to a holder can be sufficient.

In this connection, a preferred embodiment provides for the holder to have a spike-shaped central electrode by means of which the tube piece can immediately be welded together with film layers of the bag at an additional processing station of the present plant.

Therefore, it is also useful with regard to unit operations if the feeding tube is fed onto a spike, in particular on a central electrode.

If so desired, the feeding tube can immediately be heated up at the tube transfer station by means of a spike-shaped central electrode, since it has been shown that the tube piece transferred to the holder can be separated much more easily from the residual tube of the feeding tube when it has been heated.

To be more precise, by heating the feeding tube in the cutting region, the formation of residual tube material particles produced by cutting can be further reduced.

It has been shown that the tube piece to be transferred can be easily plugged onto this spike if the outer diameter of the spike is adapted to the inner diameter of the feeding tube such that the separated tube piece can preferably be held to the spike even by a frictional connection so that the cut tube piece can be safely transported from the tube transfer station to an additional processing station of the plant for manufacturing a bag.

It is advantageous, however, if the holder has an exterior tube clip so that larger tensile forces can be applied to the feeding tube as well without the risk of the tube piece to be deconnected separating from the holder or from the spike or from the spike-shaped central electrode, respectively.

If the holder is fixed into place in the feeding direction of the feeding tube, the feeding tube can be safely plugged on an accordingly stationary fixed spike or on an accordingly stationary fixed spike-shaped central electrode and tensile forces can be applied to the feeding tube without the holder moving to detriment in the feeding direction or in the main effective direction of the tensile forces, respectively.

Thus, the holder remains in a stationary position with the tube piece to be cut off fastened to it if the feeding tube is pulled in the direction opposite to feeding for application of the tensile forces.

Therefore, a preferred embodiment also provides for the feeding tube to be fixed with the holder against retraction to a tube piece to be cut off; in particular, the embodiment provides for it to be clamped to the holder from the outside.

Alternatively or cumulatively, clamping can also take place by means of a spike which can be expanded radially or a spike-shaped central electrode which can be expanded radially.

In the present application, "radially" generally means "transversely to the feeding direction of the feeding tube".

It is understood that the present transfer means can take nearly any form.

Another preferred method embodiment provides for the tube to be fed through a duct, which helps to position the end of the feeding tube facing the holder more precisely before the spike or before the spike-shaped central electrode, respectively.

For being able to guide the feeding tube more precisely when it is transferred to the holder or plugged onto the spike or onto the spike-shaped central electrode in the direction radial to the feeding direction, i.e. laterally, it is therefore advantageous if the transfer means has a duct for the feeding tube.

The feeding tube can be transferred to the holder with particular precision if the transfer means can be driven back and forth in the feeding direction.

This means, in other words, that specifically the transfer means is positioned in the tube transfer station so that it is translationally supported in a tube feeding direction and in a tube retraction direction.

A particularly preferred embodiment provides for the transfer means to be adapted to approximate the duct to the holder, then to transfer the feeding tube at least with the tube piece to be cut off, and after it has been cut off, to retract the residual tube of the feeding tube from the holder through the duct.

The tube drawing means proposed by the invention can take nearly any desired shape as well.

Advantageously, the tube drawing means has a retraction drive so that the feeding tube, which is clamped to the holder by the exterior tube clip, can be drawn in opposition to the tube feeding direction, i.e. in the tube retraction direction.

For always applying tensile forces which are sufficiently high, it is advantageous if the tube drawing means has a clip which is driven with respect to the tube pulling holding means, preferably via a coupling to the transfer means.

Especially if the clip is fastened to the transfer means, it can be translated with respect to the holder by the transfer means.

In addition, it is advantageous if the tube drawing means is adapted to apply, in cooperation with the tube pulling holding means, an expansion from 1% to 10% to the transition area from the tube piece to the residual tube between the tube drawing means and the tube pulling holding means, in particular from 2% to 6%, especially about 4%.

Especially with this degree of expansion in the defined cutting region of the feeding tube, the production of residual tube material particles can be avoided very effectively when the tube piece to be separated is cut off the residual tube of the feeding tube.

Therefore, a process is also advantageous where the tube is drawn longitudinally by between 1% and 10%, preferably from 2% to 6%, especially preferably approximately 4%.

For cutting the tube piece off the feeding tube, various means can be used, for instance a wire strap or the like.

A method of cutting the tube piece off the feeding tube which is particularly clean in the sense of the invention, even without the other features of the invention, can be guaranteed if the tube transfer station has a knife which is driven, namely from a stand-by position through the feeding tube.

By a knife driven in this manner, the tube can be easily cut through constructively.

Thus, the object of the invention is also achieved by a plant for manufacturing a bag for medical purposes, comprising a tube transfer station with a transfer means for transferring a tube fed to a tube transfer station to a holder and for cutting off there a tube piece transferred to the holder from a residual tube of the feeding tube, so as to subsequently make the tube piece connectable to two film layers for forming an access to the bag, the tube transfer station having a knife which is driven from a stand-by position through the feeding tube, with the knife being driven to being released from the residual tube after cutting, namely longitudinally in the direction of the tube or with a motion component longitudinally in the direction of the tube.

By the possibility of releasing the knife with respect to the feeding tube after cutting, the risk can be reduced of producing residual tube material particles by subsequent contact of the knife with the tube.

Advantageously, during this process, the knife is at least released from the separated tube piece, preferably, however, both from this tube piece and from the residual tube of the feeding tube.

The knife can be removed very quickly from a feeding area of the feeding tube if the knife has a tilting drive. Thus, the feeding tube can again be provided to the holder within very short time.

Also for this reason, it is advantageous if the knife is tilted for release.

Especially return of the feeding tube to the cutting area for the next cutting can take place more quickly if the tilting drive is adapted to tilt the knife away from the transfer means.

If the knife is driven to move through the tube with an incline, cutting of the feeding tube can again be improved due to an advantageous cutting angle.

The feeding tube can again be cut more advantageously if the knife has a thickness of maximally 1 mm, especially maximally 0.8 mm, preferably maximally 0.5 mm, especially preferably less than 0.2 mm.

It has been found that the danger of contamination of the feeding tube by residual tube material particles can be further reduced by making the knife thinner.

Greatly improved cutting results can already be achieved if the knife has a thickness of maximally 1 mm, especially since the knife has a very long serviceable life at this thickness.

Especially the tube transfer station can be constructed even simpler if the tube drawing means and the knife are arranged on the transfer means side and the tube pulling holding means is arranged on the holder side.

As far as the method is concerned, it is advantageous if the holder and the transfer means are moved apart from each other, especially if the transfer means is retracted and during this process the feeding tube is drawn longitudinally in the defined region for cutting.

In terms of unit operations, it is further advantageous if cutting takes place by means of a knife which is fed through the feeding tube during the tensile force acting on the defined region for cutting, so that the feeding tube follows the tensile force at least on one side, preferably on both sides, of the cut region and a gap results after cutting which is wider than the thickness of the knife.

The production of undesired residual tube material particles can be substantially reduced if the knife is heated for cutting to a temperature between 40° C. and 70° C., especially between 40° C. and 60° C., in particular around 50° C.

With the plant and the method described here, with the present invention, in particular additional means for cutting the feeding tube are not necessary so that advantageously cutting can take place without alcoholic slip additives.

Thus, additional contamination of the port of the medical bag can be reduced.

It is understood that the features of the solutions described above or in the Claims, respectively, can also combined, if desired, so that the advantages and effects to be achieved can also be obtained in a cumulative manner.

In addition, additional features, effects and advantages of the present invention are described by means of the attached drawing and by means of the following specification wherein by way of example, a tube transfer station in a plant for manufacturing a medical bag is shown and described.

Figure 1:
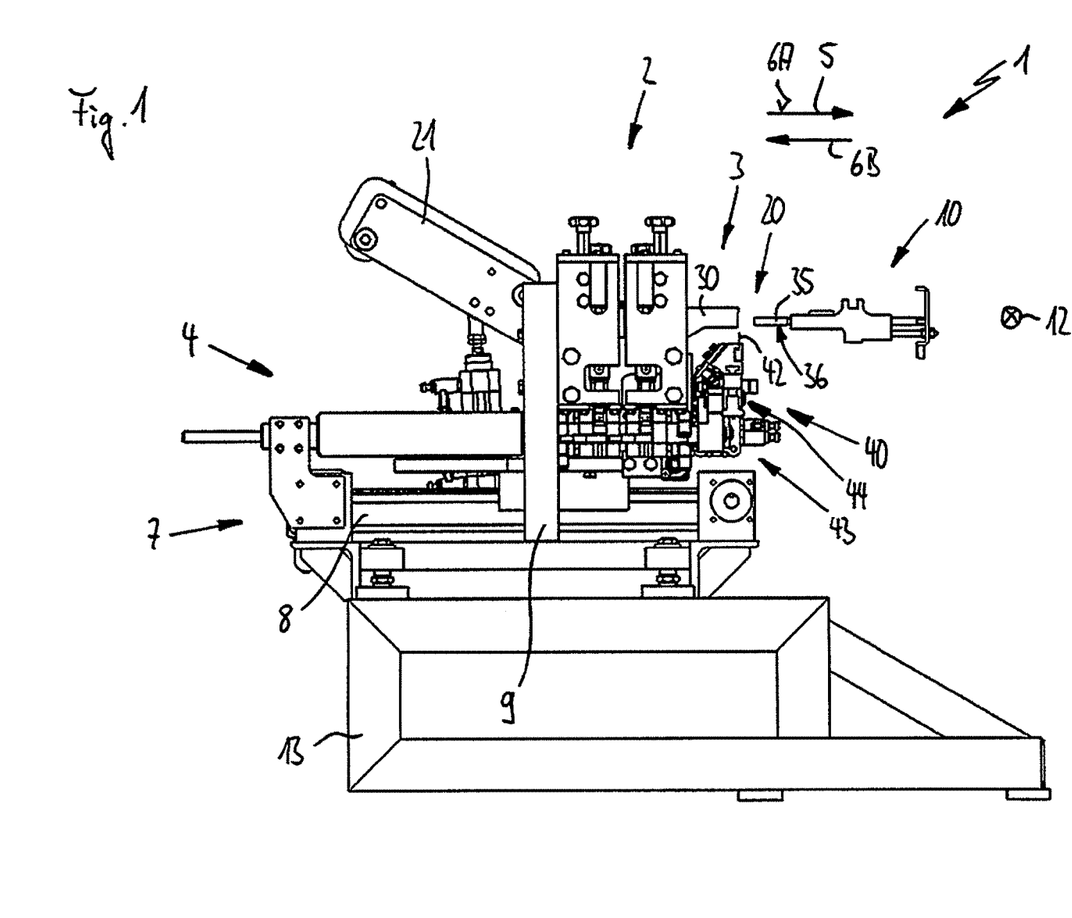
FIG. 1 schematically shows a plant for manufacturing a bag for medical purposes in a region where a tube transfer station is arranged which has, on the holder side, a tube pulling holding means and on the other side, a tube drawing means so as to be able to apply tensile forces to a feeding tube in the longitudinal direction of the tube.

The plant 1 for manufacturing a bag (not shown) for medical purposes, which plant is at least partially shown in FIG. 1, comprises, among others, a tube transfer station 2 which is schematically shown in a lateral view in the presentation in FIG. 1.

The tube transfer station 2 has a transfer means 3 which can be translated by means of a positioning mechanism 4 in the feeding direction 5 or the tube feeding direction 6A or in the tube reversal direction 6B opposite to the feeding direction 5.

This positioning mechanism 4 has at least one linear positioning device 7 with a linear crosshead 8 and a carriage part 9 on which the transfer means 3 are suspended.

Before these transfer means 3, seen in the feeding direction 5 or the tube feeding direction 6A, respectively, there is a holder 10 to which a feeding tube 11 (see FIG. 2) is to be transferred.

During this process, the holder 10 arrives, if required, before the tube transfer station 2 or before the transfer means 3, respectively (seen in the rotation direction) and is stopped such that the feeding tube 11 is transferred from the tube transfer station 2 according to the invention to the holder 10.

For this purpose, the holder 10 is guided by a circulating conveyor belt (not shown) of a conveying device (not shown) of the plant 1; the corresponding conveying unit is not further explained since it is sufficiently known from the state of the art.

The entire plant 1 is integrally connected to a floor (not shown separately) by means of a frame 13.

As shown in more detail below in connection with FIG. 8, the tube transfer station 2 is also characterized by an air inlet and air outlet unit 14 by means of which an air flow or air circulation at the tube transfer station 2 can be forced.

Figure 2:
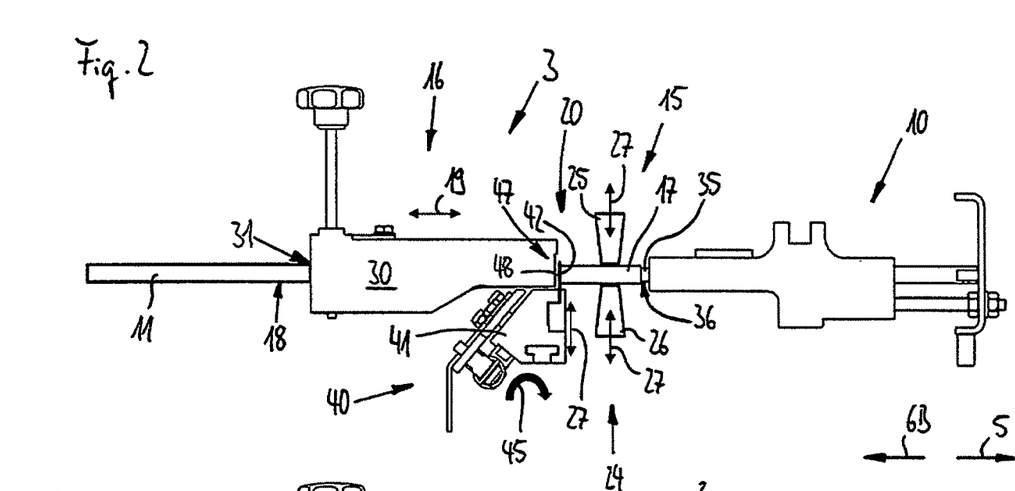
FIG. 2 schematically shows a method step in the tube plug-on station shown in FIG. 1, where a tube plugged onto a central electrode is clamped radially from outside and then pre-tensioned axially.

As can be well seen especially in the representation in FIG. 2, the present tube transfer station 2 is characterized, in any case, on the holder side, by a tube pulling holding means 15 and, on the other side, by a tube drawing means 16 which are adapted to apply tensile forces 19 between a separated tube piece 17 and a residual tube 18 of the feeding tube 11.

In particular, these tensile forces 19 are applied in the region of a cut during separation of the residual tube 18 from the tube piece 17 to be cut off, so as to achieve an improved cut or an improved cutting movement at a point 20 of cutting, which leads to a production of less or substantially less residual tube material particles (not shown here) which may contaminate the port to be created and thus also the content of the medical bag.

For application of the tensile forces 19, the tube drawing means 16 has a retraction drive 21 assigned to the transfer means 3 so that this retraction drive 21 can be moved by means of the linear positioning device 7 together with the transfer means 3.

Especially by means of the tube drawing means 16 in cooperation with the tube pulling holding means 15, the feeding tube 11 can be expanded specifically in the region of the cut 20 by 1% to 10%.

Particularly advantageous is an expansion of approximately 4% since it has been shown that in this case, the cut can be performed such that there are hardly any residual tube material particles produced during cutting.

The tube pulling holding means 15 assigned to the holder 10 comprise, at least in this embodiment, a clamping device (not referenced separately) in the form of a tube clip 24 attached from radially outside, which has in particular two clamping elements 25 and 26 which can be advanced to the tube piece 17 to be cut from radially outside, where the two clamping elements 25 and 26 are supported movably transversely with respect to the feeding direction 5, i.e. in the radial direction 27.

The tube drawing means 16, on the other hand, is supplemented, at least in this example of embodiment, by fixing elements not shown here and/or by the retraction drive 21, which are assigned to the transfer means 3.

Thus, the tube piece 17 to be cut off, which is supported by the holder 10 on one side, and the residual tube 18 of the feeding tube 11 on the other side can be fixed and supported, respectively, by the transfer means 3, wherein transfer means embodied in this way help to implement a particularly easy construction of the present tube drawing means 16.

In the present invention, the feeding tube 11 is guided laterally in a particularly precise manner on the transfer means 3 since the transfer means 3 has a basic body 30 which has at least one duct 31 for the feeding tube 11 through which the feeding tube 11 can be guided in the feeding direction 5 and thus also moved in relation to the basic body 30.

For fixing the feeding tube 11 and the tube piece 17 to be cut off securely into place for operation, the holder 10 has a spike 35 specifically in this embodiment which is formed as a spike-shaped central electrode 36 in this case.

Advantageously, the spike 35 or the spike-shaped central electrode 36, respectively, has an outer diameter (not referenced separately) which is complementary to the inner diameter (also not referenced explicitly) of the feeding tube 11 such that the feeding tube 11 fed in the tube feeding direction 6A can be safely plugged onto the spike 35 or onto the spike-shaped central electrode 36.

Especially because of this specific embodiment, the tube transfer station 2 can also be called a tube plug-on station (not referenced additionally) in this case.

The same applies to the transfer means 3 which in the present case is a plug-on means (not referenced additionally) for plugging the feeding tube 11 onto the holder 10.

The tube transfer station 2 is further assigned to a cutting device 40 which is arranged at the linear positioning device 7 together with the transfer means 3.

The cutting device 40 in this embodiment has a cutting head 41 bearing a knife 42 for cutting the feeding tube 11.

The cutting device 40 is further characterized by having on one side a lifting and lowering drive 43 and on the other side additionally a tilting drive 44.

Thus, the knife 42 cannot only be translated in the radial direction 27 with respect to the feeding direction 5 of the feeding tube 11, but by means of the tilting drive 44, the knife can also be guided along a circular path 46 in the direction of the arrow 45 (see especially FIG. 5) so as to be removed downward from the cutting place 20.

In this embodiment, by way of example, the knife 42 has a thickness of merely 0.2 mm which also has a very positive effect on the avoidance of residual tube material particles when the feeding tube 11 is cut.

In FIG. 2, the tube transfer station 2 is shown in a positioning state in which the feeding tube 11 has already been fed to the holder 10 and where the tube piece 17 to be cut off or which has already been cut off is plugged onto the spike 35 of the holder 10.

Also, the feeding tube 11 or the tube piece 17 which has already been cut off is held by the tube pulling holding means in the form of the tube clip 24 on the outside, where the feeding tube 11 is drawn longitudinally by the tube drawing means 16 and the tube piece 17 to be cut off has already been cut off from the residual tube 18 of the feeding tube 11.

The knife 42 was guided through the tube 11 while the tensile forces 19 already acted on the defined cutting place 20 so that the feeding tube 11 followed at least on one side, but preferably on both sides, the tensile forces 19 at the cutting place 20, resulting in a gap 48 after cutting which in any case was wider than the thickness of the knife 42.

Figure 3:
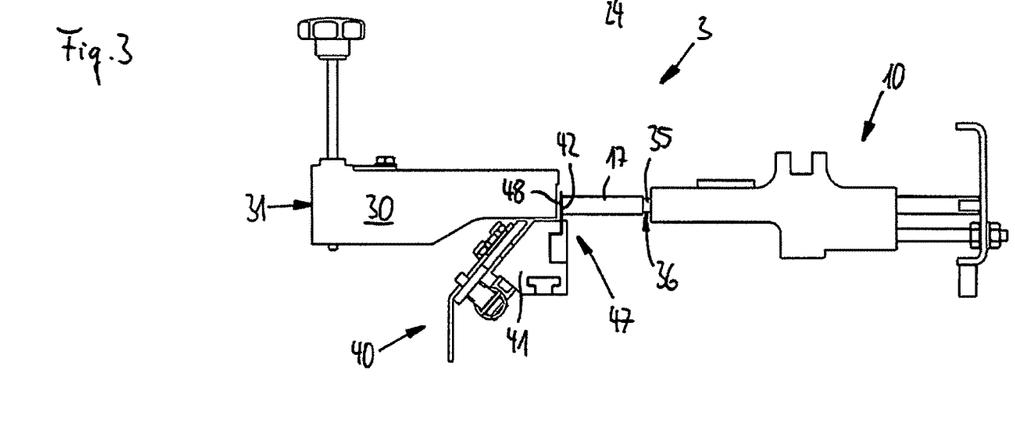
FIG. 3 schematically shows another method step in the tube plug-on station shown in FIG. 1 where the tube clamped radially from outside and pre-tensioned axially is cut.

Whereas in FIG. 2, the tube transfer station 2 is shown with the tube clip 24 activated and a feeding tube 11 which has just been cut, FIG. 3 shows a next method step of the tube transfer station 2 in which clamping elements 25 and 26 of the radially attached tube clip 24 are again retracted radially to the outside. The knife 42, however, is still in the cutting position 47.

Figure 4:
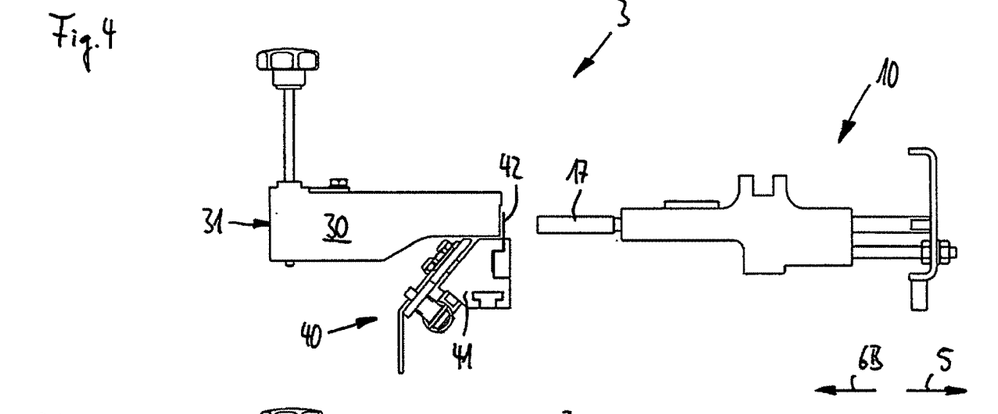
FIG. 4 schematically shows a next method step in the tube transfer station shown in FIG. 1 where the tube drawing means and the knife are axially retracted.
Figure 5:
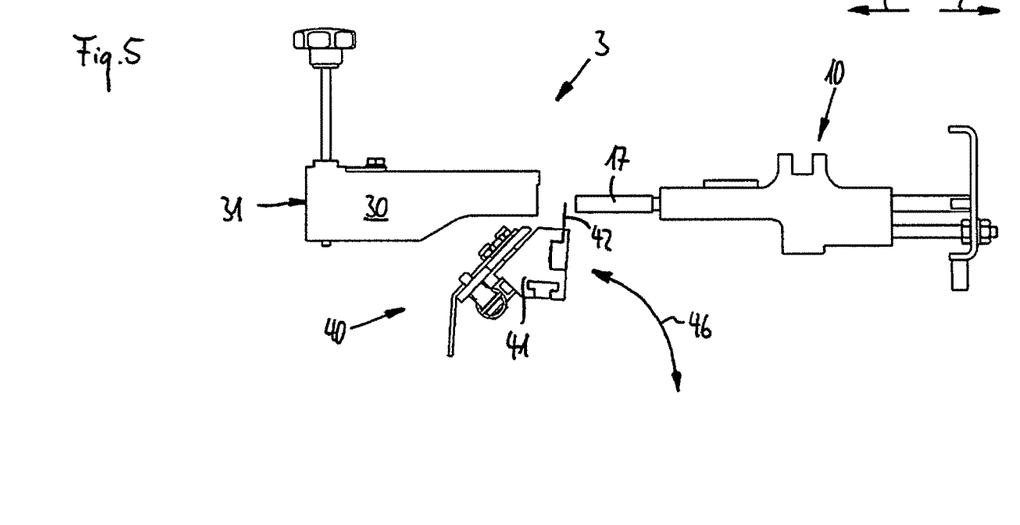
FIG. 5 schematically shows a next method step at the tube transfer station shown in FIG. 1 where the knife is folded downward radially.

According to FIG. 4, the knife 42 is released both from the tube piece 17 which has been cut off and from the residual tube 18 after cutting; on one side, by means of a translation in the tube retraction direction 6B of the transfer means 3 and on the other side, by means of a tilting movement of the knife along the circular path 46 according to FIG. 5.

Figure 6:
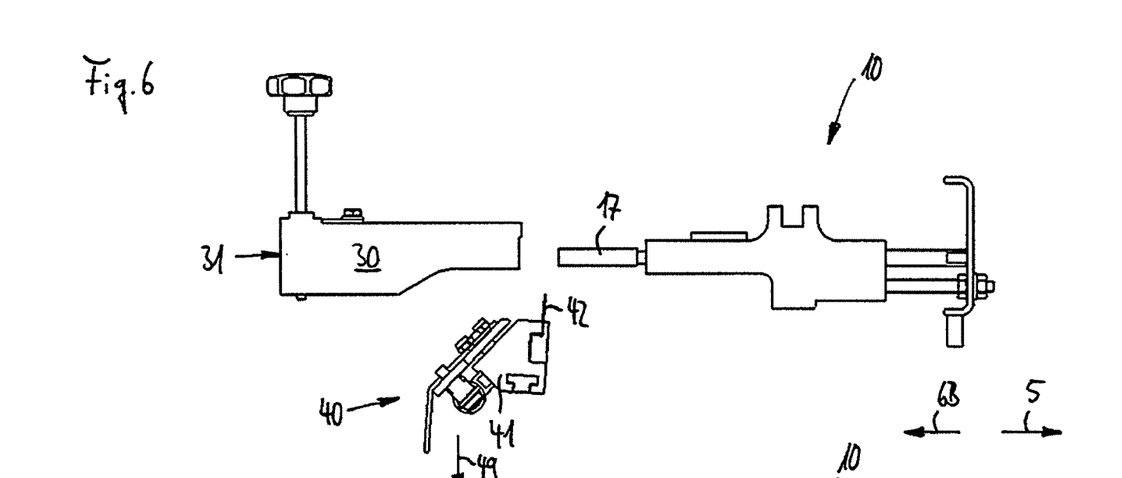
FIG. 6 schematically shows a next method step at the tube transfer station shown in FIG. 1 where the knife is moved translationally downward radially.

FIG. 6 shows the tube transfer station 2 in a next method step in which the knife 42 and the entire cutting head 41 are additionally lowered in the direction 49 by means of the lifting and lowering drive 43 so that the knife 42 is entirely moved out of the region of the cutting place 20.

Finally, in FIG. 7, the knife 42 is again tilted into a stand-by position 50 so that the feeding tube 11 can be fed to an additional holder 10 in the tube feeding direction 6A.

Figure 7:
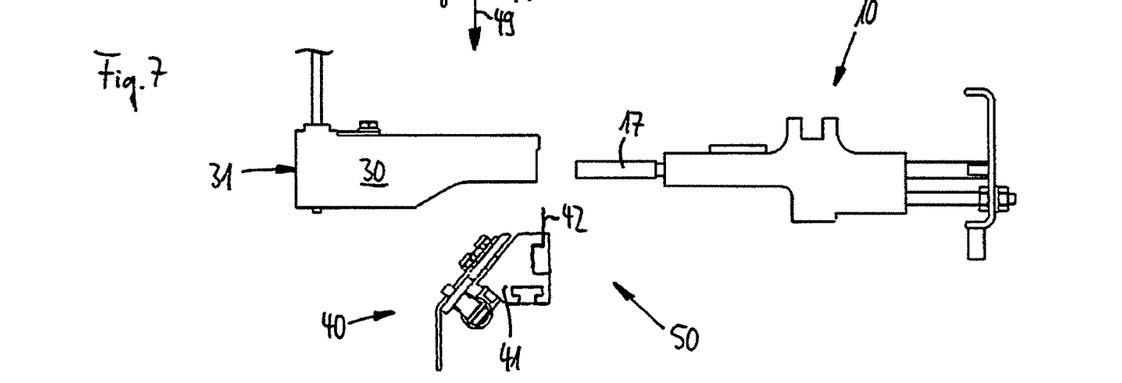
FIG. 7 schematically shows a next method step at the tube transfer station shown in FIG. 1 where the knife is again folded upward along the circular path into a stand-by position.

It is understood that after release of the knife 42 from the separated tube piece 17, the holder 10 can be advanced to an additional processing station (not shown here) of the plant 1 and that the separated tube piece 17 which is still held by the holder 10 is provided for further processing at this additional processing station.

Figure 8:
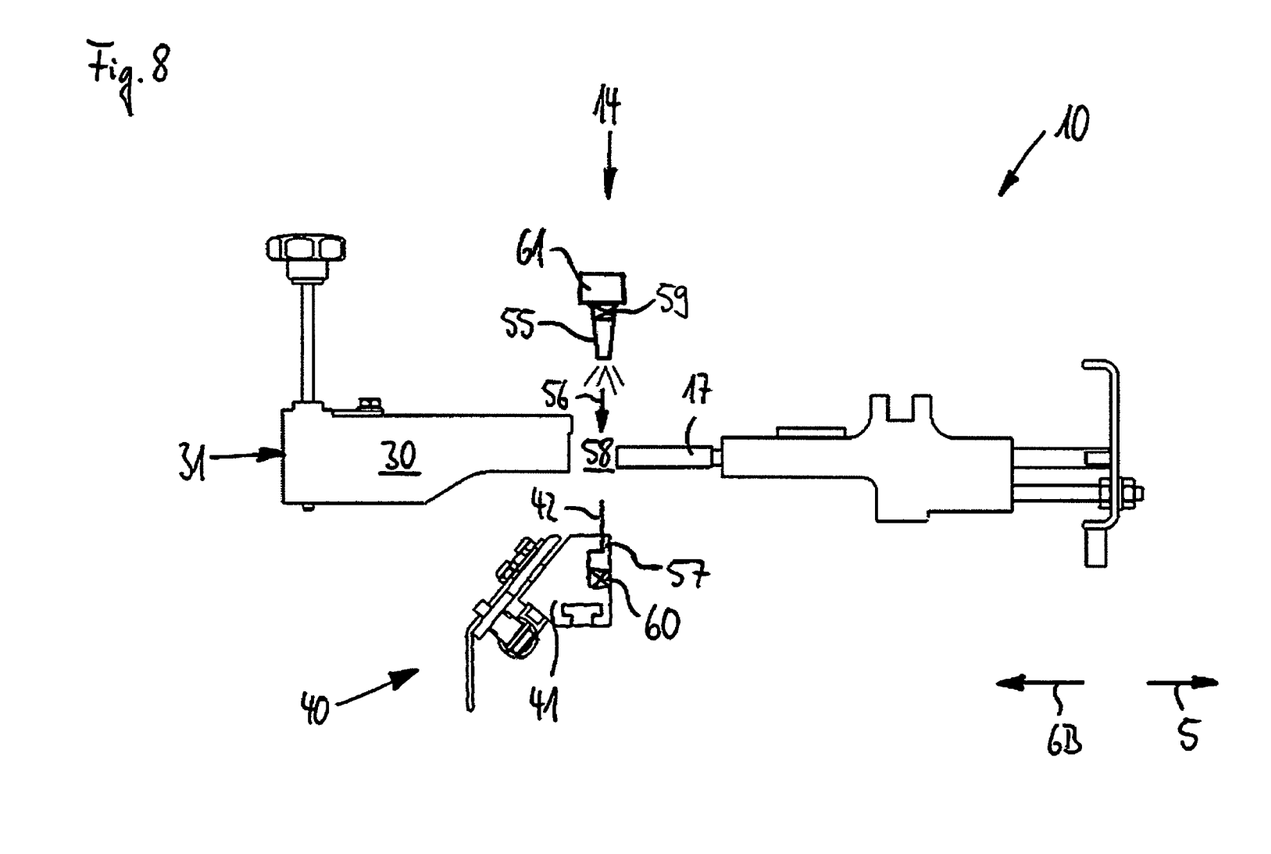
FIG. 8 schematically shows a view of the tube transfer station shown in FIG. 1 with activated air nozzles.

In FIG. 8, the air inlet and air outlet device 14 is shown in an activated state.

The air inlet and air outlet device 14 comprises at least in this example of embodiment a first air nozzle 55 for blowing out air into a region at the designated place 20 so that a forced air flow 56 flows around and into this designated place 20.

Furthermore, this first air nozzle 55 is arranged between the transfer means 3 and the holder 10.

In this example of embodiment, the air inlet and air outlet device 14 comprises also an additional air nozzle 57 for letting air in and out of the region at the designated place 20 so that the forced air flow 56 is aspirated by the additional air nozzle 57 and reinforced, if desired.

It is also conceivable for the forced air flow 56 to be generated exclusively by the additional air nozzle 57, for instance if the first air nozzle 55 is out of function or has not even been provided.

The additional air nozzle 57 is integrated directly in the cutting head 41 of the cutting unit 40, which cutting head 41 is tiltable according to the circular path 46 (see FIG. 5).

In terms of construction, the additional air nozzle 57 is simply positioned below the basic body 30 of the transfer means 3.

The additional air nozzle 57 is also arranged next between the transfer means 3 and the holder 10.

As a whole, the action area 58 (only numbered by way of example) of the two air nozzles 55 and 57 is located in particular at the height of the gap 48 produced when the feeding tube 11 is cut, or of the designated place 20.

The substantial advantage of this air inlet and air outlet device 14 is that by means of the first air nozzle 55, any residual tube material particles are blown away from the separated tube piece 17.

However, these tube material particles are not simply blown away from the region of the designated place 20 but are advantageously also aspirated immediately by means of the additional air nozzle 57 so that the tube material particles can advantageously not be released into the environment of the tube transfer station 2, or only at a greatly reduced amount.

Advantageously, the air nozzles 55 and 57 each comprise a pressure difference means 59 and 60 for producing the air flow 56, the first pressure difference means 59 comprising a blowing unit (not referenced separately) and the second pressure difference means 60 comprising an aspiration unit (not referenced separately).

For sterilization in particular of the separated tube piece 17 at the tube transfer station 2, the tube transfer station furthermore has an air ionization unit 61 which is assigned in this example of embodiment to the first air nozzle 55 so that the air flowing out of it has already been ionized.

At this point, it is explicitly pointed out that the features of the solutions described above or in the Claims and/or Figures can also be combined, if necessary, in order to implement or achieve, respectively, the described features, effects and advantages accordingly in combination.

It is understood that the example of embodiment described above only refers to a first embodiment of the plant or tube transfer station according to the invention and of the method according to the invention; therefore, the invention is not limited to this example of embodiment.

All features disclosed in the application documents are claimed as essential for the invention, provided that they are novel over the state of the art individually or in combination.

LIST OF REFERENCE NUMBERS

1 plant
2 tube transfer station
3 transfer means
4 positioning mechanism
5 feeding direction
6A tube feeding direction
6B tube retraction direction
7 linear positioning direction
8 linear crosshead
9 carriage part
10 holder
11 feeding tube
12 movement circulation direction
13 frame
14 air input and air output device
15 tube pulling holding means
16 tube drawing means
17 transferred tube piece which has been or is to be cut off
18 residual tube
19 tensile forces
20 cut or designated cutting place
21 retraction drive
24 tube clip acting from radially outside
25 first clamping element
26 second clamping element
27 radial direction
30 basic body
31 duct
35 spike
36 spike-shaped central electrode
40 cutting unit
41 cutting head or holding device, respectively
42 knife or cutting means
43 lifting and lowering drive
44 tilting drive
45 arrow
46 circular path
47 cutting position
48 gap
49 downward direction
50 standby position
55 first air nozzle
56 air flow
57 additional air nozzle
58 action area
60 first pressure difference means
61 air ionization unit

The invention claimed is:

1. Plant for manufacturing a bag for medical purposes, comprising a tube transfer station with a transfer means for transferring a feeding tube fed to the tube transfer station to a holder and for separating at the holder a separated tube piece transferred to the holder from a residual tube of the feeding tube, so as to make the separated tube piece subsequently connectable to two film layers for forming an access on the bag,
   wherein the tube transfer station comprises at least one air nozzle, an action area of the at least one air nozzle being directed at a designated place for cutting, so that an air flow forced by air which has been blown out and/or aspirated from and/or to the at least one nozzle into and/or from the designated place can be adjusted for cutting at the designated place,
   wherein the at least one air nozzle has a pressure difference means for producing an overpressure and/or a vacuum at the at least one air nozzle, so that during operation of the pressure difference means, an air flow forced by air which has been blown out and/or aspirated can be adjusted for cutting at the designated place.

2. Plant according to claim 1, wherein the at least one air nozzle comprises at least two air nozzles, of which a first air nozzle is adapted for blowing out air and a second air nozzle is adapted for aspirating air.

3. Plant according to claim 1, wherein the at least one air nozzle comprises at least two air nozzles, wherein the designated place for cutting is arranged between the at least two air nozzles.

4. Plant according to claim 2, wherein the second air nozzle for aspirating air is arranged in a sluable manner at the tube transfer station.

5. Plant according to claim 2, wherein the holder is a first holder, and the second air nozzle for aspirating air is arranged in a sluable manner at a second holder for holding a cutting means for cutting the feeding tube.

6. Plant according to claim 1, wherein the tube transfer station has a tube pulling holding means and a tube drawing means which are adapted to apply tensile forces between the separated tube piece and the residual tube while cutting takes place.

7. Plant according to claim 1, wherein the holder has a spike.

8. Plant according to claim 1, wherein the holder has a tube clip acting radially in a direction perpendicular towards a feeding direction towards the action area.

9. Plant according to claim 1, wherein the holder is fixed into place in a feeding direction of the feeding tube.

10. Plant according to claim 1, wherein the transfer means has a duct for the feeding tube.

11. Plant according to claim 1, wherein the transfer means can be driven forward and backward in a feeding direction.

12. Plant according to claim 10, wherein the transfer means is adapted to position the duct close to the holder, to then transfer the feeding tube at least with the tube piece to be separated and, after the tube piece has been cut off, to again remove the residual tube of the feeding tube from the holder through the duct.

13. Plant according to claim 6, wherein the tube drawing means has a retraction drive.

14. Plant according to claim 6, wherein the tube drawing means has a clip driven in respect to the tube pulling holding means.

15. Plant according to claim 6, wherein the tube drawing means is adapted to apply, in cooperation with the tube pulling holding means, an expansion of 1% to 10% to the transition from the tube piece to be separated to the residual tube between the tube drawing means and the tube pulling holding means of 2% to 6%.

16. Plant according to claim 1, wherein the tube transfer station has a knife which is actuated from a standby position through the feeding tube.

17. Plant according to claim 16, wherein the knife is driven from the standby position through the feeding tube, with the knife being driven to release itself from the residual tube after separation longitudinally in a tube direction or with a motion component longitudinally in the tube direction.

18. Plant according to claim 16, wherein the knife has a tilting drive.

19. Plant according to claim 18, wherein the tilting drive is adapted to tilt the knife away from the transfer means.

20. Plant according to claim 16, wherein the knife is driven to move slantingly through the tube.

21. Plant according to claim 16, wherein the knife has a thickness of maximally 1 mm.

22. Plant according to claim 16, further comprising a tube drawing means and a tube pulling holding means, wherein the tube drawing means and the knife are arranged on a transfer side whereas the tube pulling holding means is arranged on a holder side different from the transfer side.

23. Plant according to claim 7, wherein the holder has a spike-shaped central electrode.

24. Plant according to claim 14, wherein the clip is driven via a coupling to the transfer means.

25. Plant according to claim 21, wherein the knife has a thickness of maximally 0.8 mm.

26. Plant according to claim 21, wherein the knife has a thickness of maximally 0.5 mm.

27. Plant according to claim 21, wherein the knife has a thickness of less than 0.2 mm.

* * * * *